(12) United States Patent
Hage et al.

(10) Patent No.: US 9,469,666 B2
(45) Date of Patent: Oct. 18, 2016

(54) PREPARATION OF BLEACHING CATALYSTS

(75) Inventors: Ronald Hage, Leiden (NL); Jianrong Zhang, Shanghai (CN); Wei Zhao, Shanghai (CN)

(73) Assignee: Catexel Limited, London (GB)

(*) Notice: Subject to any disclaimer, the term of this patent is extended or adjusted under 35 U.S.C. 154(b) by 795 days.

(21) Appl. No.: 13/582,040

(22) PCT Filed: Mar. 3, 2010

(86) PCT No.: PCT/CN2010/000256
§ 371 (c)(1),
(2), (4) Date: Nov. 13, 2012

(87) PCT Pub. No.: WO2011/106906
PCT Pub. Date: Sep. 9, 2011

(65) Prior Publication Data
US 2013/0053554 A1    Feb. 28, 2013

(51) Int. Cl.
C07F 13/00    (2006.01)

(52) U.S. Cl.
CPC .................................. C07F 13/005 (2013.01)

(58) Field of Classification Search
None
See application file for complete search history.

(56) References Cited

U.S. PATENT DOCUMENTS

| | | | |
|---|---|---|---|
| 5,153,161 A | 10/1992 | Kerschner et al. | |
| 5,256,779 A | 10/1993 | Kerschner et al. | |
| 5,274,147 A | 12/1993 | Kerschner et al. | |
| 5,329,024 A | 7/1994 | Jureller et al. | |
| 5,356,554 A | 10/1994 | Delwel et al. | |
| 5,429,769 A | 7/1995 | Nicholson et al. | |
| 5,516,738 A | 5/1996 | Jureller et al. | |
| 5,756,727 A | 5/1998 | Beller et al. | |
| 6,087,312 A | 7/2000 | Masotti et al. | |
| 6,432,900 B1 | 8/2002 | Appel et al. | |
| 7,972,386 B2 | 7/2011 | de Almeida et al. | |
| 7,976,582 B2 | 7/2011 | de Almeida et al. | |
| 8,455,423 B2 | 6/2013 | Hage et al. | |
| 2001/0025695 A1 | 10/2001 | Patt et al. | |
| 2002/0010120 A1 | 1/2002 | Hage et al. | |
| 2002/0066542 A1 | 6/2002 | Jakob et al. | |
| 2002/0160925 A1 | 10/2002 | Hage et al. | |
| 2003/0040459 A1 | 2/2003 | Araya et al. | |
| 2005/0137105 A1 | 6/2005 | Griese et al. | |
| 2005/0137118 A1 | 6/2005 | Silveri | |
| 2006/0277687 A1 | 12/2006 | Buhler et al. | |
| 2009/0205143 A1 | 8/2009 | Hage et al. | |
| 2012/0202990 A1 | 8/2012 | Reinhardt et al. | |
| 2012/0302490 A1 | 11/2012 | Reinhardt et al. | |

FOREIGN PATENT DOCUMENTS

| | | | |
|---|---|---|---|
| DE | 19523891 C1 | 11/1996 | |
| EP | 0458398 | 5/1991 | |
| EP | 0458397 | 11/1991 | |
| EP | 0509878 | 4/1992 | |
| EP | 0530870 | 7/1992 | |
| EP | 509787 | * 10/1992 | ............... C11D 3/39 |
| EP | 0 544 491 | 11/1992 | |
| EP | 0544490 | 11/1992 | |
| JP | 2007-112761 | 5/2007 | |
| WO | WO 93/25562 | 12/1993 | |
| WO | WO 94/05422 | 3/1994 | |
| WO | WO 95/27773 | 10/1995 | |
| WO | WO 95/30733 A1 | 11/1995 | |
| WO | WO 96/06154 A1 | 2/1996 | |
| WO | WO 97/44520 | 11/1997 | |
| WO | WO 01/64697 | 9/2001 | |
| WO | WO 01/64993 | 9/2001 | |
| WO | WO 02/064721 | 8/2002 | |
| WO | WO 02/088063 | 11/2002 | |
| WO | WO 2005/033070 | 4/2005 | |
| WO | WO 2006/125517 | 11/2006 | |
| WO | WO 2011/066934 A1 | 6/2011 | |

OTHER PUBLICATIONS

Koek J H et al., "Synthesis and properties of hydrophobic [MnIV 2 (m-O)3(L)2]2+ complexes, derived from alkyl substituted 1,4,7-triazacyclononane ligands et al.," Inorganica Chimica Acta, 295(2), 189-199 (1999).

Schafer K-O et al., "Electronic Structure of Antiferromagnetically Coupled Dinuclear Manganese (MnIIIMnIV) Complexes Studied by Magnetic Resonance Techniques" J. Am. Chem. Soc., 120(50), 13104-13120 (1998).

Wieghardt K et al., "Synthesis, Crystal Structures, Reactivity, and Magnetochemistry of a Series of Binuclear Complexes of Manganese( 11), -( 111), and -( IV) of Biological Relevance. The Crystal Structure of [ L'M~'"(~L-O)~M~~~L'](PF~)~Containing an Unprecedented Short Mn—Mn Distance of 2.296 A" J. Am. Chem. Soc., 110(22), 7398-7411 (1988).

PCT International Search Report and Written Report re International Application No. PCT/CN2010/000256 Mailed on Dec. 9, 2010 in 10 pages.

Romakh, et al. "Dinuclear Manganese complexes containing 1,4-dimethyl-1,4,7-triazacyclononane ligands as well as carboxylate and oxo bridges" Inorganica Chimica Acta 359, 2006, pp. 1619-1626.

Koek, et al. "Improved syntheses, structures, spectral and electrochemical properties of $[Mn1_2(u-O_2CMe)_2L_2]^{2+}$ and $[Mn^{IV}_2(u-O)_3L_2]^{2+}$ complexes. Two homologous series derived from either N-substituted 1,4,7-triazacyclononanes" J. Chem. Soc., 1996, pp. 353-362.

European Search Report from related European Application No. 10846825.7 dated Sep. 23, 2013 in 7 pages.

Hage et al., "Efficient Manganese Catalysts for Low-Temperature Bleaching", Nature, Jun. 23, 1994, vol. 369, pp. 637-639.

EP Search Report in EP Application No. EP 05 25 3295.

PCT International Search Report in PCT Application No. PCT/EP2006/004260 mailed Jul. 28, 2006.

I Garcia-Bosch et al. (Organic Letters, Oct. 2008, 2095-2098).

BC Gilbert et al. (Org. Biomol. Chem., Jan. 2003, 1568-1577).

(Continued)

Primary Examiner — Noble Jarrell
(74) Attorney, Agent, or Firm — Knobbe, Martens, Olson & Bear, LLP

(57) ABSTRACT

The present invention concerns synthesizing manganese complexes in essentially non-aqueous solutions.

24 Claims, No Drawings

(56) References Cited

OTHER PUBLICATIONS

BC Gilbert et al. (J. Mol. Catal. A, 2004, 219(1), 265-272).
BC Gilbert et al. (Org. Biomol. Chem., Feb. 2004, 1176-1180).
G Reinhardt (J. Mol. Catal. A: Chemical, 2006, 251, 177-184).
T Wieprecht et al. (J. Surfactants and Detergents, 2004, 7(1), 59-66).
Wieghardt, Karl et al., "Assembly and Structural Characterization of Binuclear u-Oxo-u-acetato Bridged Complexes of Manganese(m). Analogues of the Di-iron(m) Centre in Hemerythrin", J. Chem. Soc. Chem. Commun., pp. 347-349, 1985.

* cited by examiner

PREPARATION OF BLEACHING CATALYSTS

FIELD OF INVENTION

The invention concerns the synthesis of bleach and oxidation catalysts in non-aqueous solutions.

BACKGROUND OF THE INVENTION

Wieghardt et al, in JACS, 110, 7398 (1988) describe the synthesis of $[Mn^{IV}{}_2(\mu\text{-}O)_3(Me_3\text{-}TACN)_2](PF_6)_2$ by reacting a dinuclear bis-carboxylate bridged $Me_3$-TACN manganese (III) complex in ethanol/water mixture and air (dioxygen) ($Me_3$-TACN=1,4,7-trimethyl-1,4,7-triazacyclononane).

Wieghardt et al, in JACS, 120, 13104 (1998) describe the synthesis of $[Mn^{IV}Mn^{III}(\mu\text{-}O)_2(\mu\text{-}OAc)(Me_4\text{-}DTNE)](ClO_4)_2$ by reacting Mn(III) acetate in methanol and allow slow aerial oxidation to form the complex ($Me_4$-DTNE=1,2-bis-(4,7-dimethyl-1,4,7-triazacyclonon-1-yl)-ethane).

Koek et al., in Inorg Chim Acta, 295, 189 (1999) describe the synthesis of dinuclear Mn(IV) complexes based on TACN derivatives using water/ethanol mixtures.

WO96/06154 describes the synthesis of $[Mn^{IV}Mn^{III}(\mu\text{-}O)^2(\mu\text{-}OAc)(Me_4\text{-}DTNE)](PF_6)_2$ by reacting Mn(II) acetate tetrahydrate in ethanol/water in the presence of $KPF_6$, after which hydrogen peroxide/NaOH was added and subsequently neutralised using acetic acid.

WO2006/125517 discloses the preparation in aqueous media and use of manganese complexes with 1,4,7-Trimethyl-1,4,7-triazacyclononane ($Me_3$-TACN) and 1,2-bis-(4,7-dimethyl-1,4,7-triazacyclonon-1-yl)-ethane ($Me_4$-DTNE) as highly-water soluble salts in bleaching.

U.S. Pat. No. 5,274,147, to Unilever, discloses the formation of tri-mu-oxo bridged manganese complexes containing $Me_3$-TACN carried by treatment of dinuclear bis-carboxylate bridged complexes in aqueous ethanol solutions.

U.S. Pat. No. 5,153,161, to Unilever, discloses the formation of tri-mu-oxo bridged manganese complexes containing $Me_3$-TACN carried by treatment of aqueous solutions of ligand with manganese salts and hydrogen peroxide.

U.S. Pat. No. 5,256,779, to Unilever, discloses the formation of tri-mu-oxo bridged manganese complexes containing $Me_3$-TACN carried by treatment of aqueous solutions of ligand with manganese salts and hydrogen peroxide.

WO 2005/033070, to BASF, discloses the addition of an aqueous solution of Mn(II)acetate to an aqueous solution of $Me_3$-TACN followed by addition of a organic substrate followed by addition of hydrogen peroxide.

SUMMARY OF INVENTION

Dinuclear manganese complexes with $Mn^{III}$ and $Mn^{IV}$ ions and triazacyclononane ligands are formed by allowing the manganese salts (often as $Mn^{II}$ salts) to react with the ligand in non-aqueous solvents under inert conditions (nitrogen or argon atmosphere), after which hydrogen peroxide is added to form the high-valent $Mn^{III}$ and/or $Mn^{IV}$ species.

We have found that there is an advantage in both yield and purity of making these dinuclear manganese complexes with TACN moieties using non-aqueous solvents rather than using alcohol/water mixtures as taught in the prior art.

A further advantage is that using low-water containing media allows easy drying of the metal complex salts, even if non-coordinating anions are used that give rise to complexes that do not easily crystallize from water, such as found for $PF_6$-containing complexes. Examples of such non-coordinating counter ions include, but are not limiting to, chloride, nitrate, benzoate, sulfate, and acetate. Apart from non-coordinating, the preferred complexes also contain co-ordinating counter-ions. For ($Me_3$-TACN) the co-ordinating counter ions are three $O^{2-}$ and for $Me_4$-DTNE the co-ordinating counter ions are two $O^{2-}$ and one carboxylate ion, with acetate being the preferred one.

In one aspect the present invention provides a method of synthesising a dinuclear manganese catalysts salts from a ligand of formula (I):

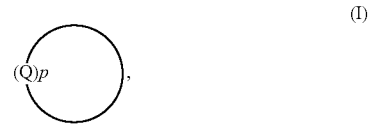

wherein:

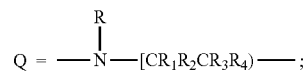

p is 3;
R is independently selected from: hydrogen, C1-C6-alkyl, $CH_2CH_2OH$, and $CH_2COOH$, or one of R is linked to the N of another Q via an ethylene bridge; R1, R2, R3, and R4 are independently selected from: H, C1-C4-alkyl, and C1-C4-alkylhydroxy, the method comprising the following steps:

(i) treating a 0.03 mmol/ml to 4 mmol/ml solution of the ligand in a solvent, with a manganese salt to form a complexation mixture, wherein the ratio of three nitrogen ring per ligand to a manganese salt is from 0.8:2 and the complexation mixture contains from 0 to 6 wt % of water;

(ii) treating the solution of step (i) with hydrogen peroxide or a source of hydrogen peroxide to provide from 1 to 10 mole $H_2O_2$ per mole of the manganese salt;

(iii) treating the solution of step (ii) with base to provide a solution having a pH of from 8 to 13;

(iv) treating the solution of step (iii) with acid to provide a solution having a pH of from 4 to 9.

It is preferred that the solution after completion of step (iv) contains from 0 to 20 vol % water, preferably from 0 to 10 vol % water.

The rate of formation of the transition metal catalyst as described in steps (i), (ii) and (iii) above, depends upon the ligand. The formation of a transition metal catalyst from $Me_3$-TACN ligand is typically complete within 5 min. Preferably the complexation mixture is left, optionally under stirring, for at least 20 minutes at a temperature in the range from 20° C. to 80° C. before step (ii) is undertaken. The formation of a transition metal catalyst from $Me_4$-DTNE ligand requires about 20 to 30 min for optimal complexation. After complex formation $H_2O_2$/base may be slowly added to form a desired Mn(IV)/Mn(IV) or Mn(IV)/Mn(III) species (steps (ii), (iii) and (iv)). This second step, the oxidation step, provides a sufficiently stable complex for storage as solid material or dissolved in an aqueous or non-aqueous solution.

In another aspect the present invention provides the preformed transition metal catalyst salt as defined herein, wherein the preformed transition metal catalyst salt has been formed by a contact and oxidation step that is carried out at least 24 hours previously, preferably 7 days previously, and is stored in a closed, preferably sealed, container.

DETAILED DESCRIPTION OF THE INVENTION

The ligand of the transition metal catalyst is of formula (I):

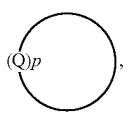

wherein:

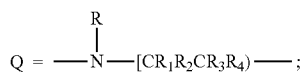

p is 3;

Preferably R is independently selected from: hydrogen, $CH_3$, $C_2H_5$, $CH_2CH_2OH$ and $CH_2COOH$; least preferred of this group is hydrogen. Most preferably R is Me and/or one of R is an ethylene bridge linking the N of Q to the N of another Q. Preferably R1, R2, R3, and R4 are independently selected from: H and Me. Preferred ligands are 1,4,7-trimethyl-1,4,7-triazacyclononane ($Me_3$-TACN) and 1,2-bis-(4,7-dimethyl-1,4,7-triazacyclonon-1-yl)-ethane ($Me_4$-DTNE) of which $Me_3$-TACN is most preferred. The manganese ion is most preferably Mn(III) and/or Mn(IV).

Co-ordinating counter ions for the transition metal complexes are $O^{2-}$ and/or carboxylate (preferably acetate). It is preferred that the transition metal complexes have at least one $O^{2-}$ co-ordinating counter ion. In particular, for $Me_3$-TACN three $O^{2-}$ co-ordinating counter ions are preferred or one $O^{2-}$ co-ordinating counter ion and two carboxylate co-ordinating counter ions are preferred, with two acetate moieties as co-ordinating counter ions being most preferred.

For $Me_4$-DTNE two $O^{2-}$ co-ordinating counter ions and one acetate co-ordinating counter ion are preferred.

The non-coordinating anion of the transition metal catalyst salt is preferably selected from the group consisting of chloride, acetate, benzoate, sulphate, and nitrate, perchlorate, hexafluorophosphate.

The first step of the complexation process entails dissolution of the ligand in an non-aqueous solvent, after which the manganese salt is added. Suitable and preferred solvents include, but are not limited to, methanol, ethanol, acetonitrile, toluene, acetone, dimethylsulfoxide, dimethylformamide, dichloromethane, tetrahydrofuran, dioxane, ethylene glycol, propylene glycol, 1-propanol, 2-propanol, 1-butanol, 2-butanol, and iso-butanol. OH-containing solvents are preferred, such as methanol, ethanol, 1-propanol, 2-propanol, 1-butanol, 2-butanol, iso-butanol, ethylene glycol, 1,3-propylene glycol, and 1,2-propylene glycol.

Manganese salts to be employed for the complexation steps are selected from manganese(II)chloride, manganese(II)sulphate, manganese(II)acetate, manganese(III)acetate, manganese(II)nitrate.

When $Me_4$-DTNE type complexes are synthesised and the starting material is not manganese(II) acetate or manganese (III) acetate, additionally carboxylic acid or its alkali salt thereof needs to be added in a slight excess of molar equivalent to the ligand. Preferably the alkali carboxylate is selected from sodium acetate, potassium acetate, sodium formate, potassium formate, sodium benzoate, sodium propionate and the carboxylic acid is selected from acetic acid, formic acid, benzoic acid, and propionic acid. Most preferred are sodium acetate and acetic acid.

In the subsequent step hydrogen peroxide needs to be added. Different sources of hydrogen peroxide can be used, such as aqueous hydrogen peroxide, from 3 to 70%, alkali peroxide, urea-hydrogen peroxide, sodium perborate and sodium percarbonate.

The optimal amount of peroxide is molar equivalent to the ligand, but applying a slight excess to this amount will not cause major reduction in yields.

It should be noted that introduction of water upon addition of aqueous hydrogen peroxide is essentially unavoidable. However, using concentrated hydrogen peroxide (more than 30%), will result in a level of water that is less than 10 volume %. For this reason the most preferred range of hydrogen peroxide is from 20 to 55% but hydrogen peroxide is aqueous hydrogen peroxide of from 3 and 70 wt % is acceptable.

Also additional base needs to be added to allow hydrogen peroxide to oxidise the manganese ions. The molar amount of base is approximately similar to the molar amount of peroxide added. NaOH, KOH, and other alkali hydroxides can be employed, with NaOH and KOH being most preferred. Aqueous solutions can be employed (e.g. 5 M solutions) to be added dropwise to the reaction mixtures. Alternatively, solutions of e.g. KOH in ethanol can be used, to lower the amount of water being present in the reaction medium. Furthermore, Na or K can be added to the neat alcohol solutions, generating the alkali salts of alcohols, which is then slowly added to the reaction medium.

After this process, an acid needs to be added to obtain a neutral solution (pH of from 4 to 9). Although any organic or inorganic acid will be employable, it is preferred to use the same acid as the salt of the intended complex, for example, when the chloride salt is prepared, one uses hydrochloric acid, etc Finally, one could opt to add an additional counterion salt or acid to generate the complex with larger non-coordinating counter ions. These compounds are selected from benzoate salts, benzoic acid, $NaPF_6$, $KPF_6$, $HPF_6$, and $NaClO_4$, with sodium benzoate and $KPF_6$ being preferred.

Various sources of water can be still found in the reaction medium, such as aqueous hydrogen peroxide (from 3 to 70% $H_2O_2$ is used), base added (eg 5 M NaOH in water), acid added (eg 37% HCl in water). Using the more concentrated solutions (eg more than 30% $H_2O_2$, KOH dissolved in ethanol or sodium ethanoate), concentrated acid solutions to neutralise the solutions (eg pure acetic acid), will render the water level low. Preferably the reaction medium contains less than 20% water and more preferably less than 10% water. After the reaction is completed and one wishes to obtain a solid material, the solvent needs to be removed from the solution containing the catalyst salt. Different manners to achieve this can be used, i.e. via evaporation at ambient pressure, via removal via evaporation at reduced pressure, via freeze drying, via spray drying. It will be clear for the skilled person in the art, that lower levels of water in the reaction medium will facilitate the removal of the solvent, thereby reducing the temperature and time needed to dry the material. Apart from economical reasons, also decreased change of decomposition of some of the complex will be obtained.

Alternatively one could produce the catalyst salt in solution and not isolate it as solid material. The level of catalyst salt will be then from 0.01 to 50 wt %, more preferably from 0.1 to 20 wt %, and most preferably from 0.5 to 10 wt % of the catalyst. Preferably solvents having a not very low boiling point are used if the catalyst is to remain in the solution. Non-limiting examples include ethylene glycol, propylene glycol, 1-propanol, 2-propanol, 1-butanol, 2-butanol, and iso-butanol.

Alternatively, one could produce the catalysts in a non-aqueous solvent that is poorly miscible with water (the non-aqueous solvent has a solubility in water of less than 20 g/L at 20° C.). After the complexation procedure as described in detail above to form the dinuclear complexes, water is added and mixed thoroughly to dissolve the catalyst in the aqueous phase. The aqueous phase containing the catalyst is then removed from the solvent. The amount of water applied for the extraction of the catalyst determines the concentration of the catalyst in the aqueous solution after separation from the organic phase. Preferred ranges of catalyst in water (w/w %) are from 0.01 to 50 wt %, more preferably from 0.1 to 20% and even more preferably from 0.5 to 10%. The solubility of water in dichloromethane is 13 g/L and solubility of water in toluene is 0.47 g/L (both at 20° C.).

Where the catalyst is produced in a non-aqueous solvent that is poorly miscible with water, toluene and dichloromethane are preferred. After addition of water it is preferred that the aqueous catalyst solution comprises from 0.1 and 20 wt % of the dinuclear manganese catalyst salt, preferably 0.5 to 10 wt %.

It is preferred that the solution containing the catalyst contains from 0.01 to 50 wt % of the catalyst, preferably from 0.1 to 20 wt %, more preferably from 0.5 to 10 wt %.

Although not strictly necessary, it is preferred that the complexation is carried in oxygen-free atmospheres, preferably under nitrogen or argon. Also it is preferred to store the solid material or the solution containing the catalyst under nitrogen or argon gas.

In the bleaching process it is preferred that the substrate is contacted with from 0.1 to 100 micromolar of the pre-formed transition metal catalyst and from 5 to 1500 mM of hydrogen peroxide.

Preferably the preformed transition metal catalyst salt and hydrogen peroxide are mixed just before introduction to the substrate.

EXPERIMENTAL

Example 1

Preparation of [Mn$_2$($\mu$-O)$_2$($\mu$-CH$_3$COO)(Me$_4$-DTNE)]Cl$_2$ According to Methods Known in the Prior Art (Comparative Examples)

Under N$_2$, to Me$_4$-DTNE (95% purity, 4 mmol) in different solvents (40 mL), solid mixture of MnCl$_2$.4H$_2$O (99% purity, 8.8 mmol) and sodium acetate (99% purity, 2 mmol) were added. The mixture was stirred for 30 min at 58° C. After another stirring for 10 min cooled in an ice water bath, the freshly prepared mixture of 1 M of H$_2$O$_2$ in water (9 mL, 9 mmol) and 1.5 M of NaOH (4.5 mL, 6.75 mmol) was added drop-wise over 5 min. The mixture turned immediately dark green-brown. The mixture was stirred for 20 min in an ice water bath and then for 20 min at room temperature. 1 M of acetic acid (2.5 mmol) was added. After stirring for another 20 min, the mixture was filtered to remove brown solid and the filtering bed was washed with ethanol. Then the green filtrate was evaporated (the water bath temperature <45° C.). The residual dark green oil was co-evaporated with ethanol and ethyl acetate to facilitate the removal of most of the remaining water. Dark green oils were taken up in ethanol (20 mL), and the insoluble white salts separated by filtration were washed with ethanol. After removing all ethanol, the dark green oil was obtained again. The small amount of ethanol was added and stirred for 2 min. Then the large amount of ethyl acetate was added. The green solid was precipitated immediately. After 3 hours at −20° C., the suspension was filtered off, with obtaining a green solid, which was washed with ethyl acetate, n-hexane, and dried under vacuum at 45° C. for 5 hrs to afford dark green powder as [(Mn$_2$($\mu$-O)$_2$($\mu$-OAc)(Me$_4$-DTNE)]Cl$_2$.H$_2$O.

1.1 EtOH/H$_2$O (2:1, v/v) Benchmark

Ethanol/water (2:1, v/v): 40 mL; yielding a green powder, UV-Vis purity of 85.3%, and the yield of 88%.

UV-Vis spectrum ($\epsilon$: mol$^{-1}$·L·cm$^{-1}$, in water, Mw: 630): 271 nm (11794), 554 nm (258), 639 nm (275).

IR (KBr pellet): 3421 br, 2921w, 1604m, 1568m, 1499w, 1463s, 1395s, 1337w, 1286w, 1159w, 1076w, 1057w, 1032w, 1004w, 985w, 912w, 779w, 744w, 678m, 614m cm$^{-1}$.

UPLC analysis confirmed the 12.45% of free [H$_2$(Me$_4$-DTNE)]Cl$_2$.

Total chloride amount was 13.10%.

Water analysis (Karl-Fischer method): Anal. calcd. for [(Mn$_2$($\mu$-O)$_2$($\mu$-OAc)(Me$_4$-DTNE)]Cl$_2$.H$_2$O: 2.86%; Found: 4.10%.

This example shows that the complex can be synthesised in a reasonable yield and purity, but it does contain a significant amount of uncomplexed ligand and water. This shows that the complexation procedure was not optimal.

1.2 H$_2$O, Benchmark

Demineralised water: 40 mL; yielding a green powder, UV-Vis purity of 63.8%, and the yield of 54%.

UV-Vis spectrum ($\epsilon\square$: mol$^{-1}$·L·cm$^{-1}$, in water, Mw: 630): 271 nm (8100), 554 nm (209), 639 nm (208).

IR (KBr pellet): 3425 br, 2921m, 1604m, 1567m, 1497w, 1463s, 1394s, 1338m, 1293w, 1159w, 1076w, 1057w, 1032w, 1004m, 985w, 912w, 779w, 744w, 678m, 613m cm$^{-1}$.

UPLC analysis confirmed the amount of free [H$_2$(Me$_4$-DTNE)]Cl$_2$ was 6.79%.

Total chloride amount was 12.22%.

Water analysis (Karl-Fischer method): Anal. calcd. for [(Mn$_2$($\mu$-O)$_2$($\mu$-OAc)(Me$_4$-DTNE)]Cl$_2$.H$_2$O: 2.86%; Found: 4.30%.

Similar to example 1.1, the solid material contains significant amounts of uncomplexed ligand and water. Furthermore, the yield leaves room for improvement.

Example 2

Preparation of Solid [Mn$_2$($\mu$-O)$_2$($\mu$-CH$_3$COO)(Me$_4$-DTNE)]Cl$_2$ Using Non-Aqueous Solvents for Complexation Under N$_2$, to Me$_4$-DTNE (95% purity, 4 mmol) in different solvents (10 mL to 40 mL), solid mixture of MnCl$_2$ (99% purity, 8.8 mmol) and sodium acetate (99% purity, 2 mmol) were added. The mixture was stirred for 30 min at 58° C. (as for CH$_2$Cl$_2$, 40° C. for 30 min). After another stirring for 10 min cooled in an ice water bath, the freshly prepared mixture of 1 M of H$_2$O$_2$ in water (9 mL, 9 mmol) and 5 M of NaOH (1.35 mL, 6.75 mmol) was added drop-wise over 5 min. The mixture turned immediately dark green-brown. The mixture was stirred for 20 min in an ice water bath and then for 20 min at room temperature. Glacial acetic acid (2.5 mmol) was added. After stirring for another 20 min, the mixture was filtered to remove brown solid and the filtering bed was washed with ethanol. In each case, the solvent in the green solution were evaporated (the water bath temperature <45° C.), with obtaining dark green oil, which were taken up in ethanol (20 mL). The insoluble white salts separated by filtration were washed with ethanol. After removing all ethanol, the dark green oil was obtained again. The small amount of ethanol was added and stirred for 2 min. Then the large amount of ethyl acetate was added. The green solid was precipitated immediately. After 3 hours at −20° C., the suspension was filtered off, with obtaining a green solid, which was washed with ethyl acetate, n-hexane, and dried under vacuum at 45° C. for 5 hrs to afford dark green powder as $[Mn_2(\mu\text{-}O)_2(\mu\text{-}CH_3COO)(Me_4\text{-}DTNE)]Cl_2 \cdot H_2O$.

2.1 Ethanol as Solvent

Ethanol: 10 mL: a green powder was isolated having a UV-Vis purity of 100%, and the yield of 96.3%.

UV-Vis spectrum ($\epsilon\square$: $mol^{-1} \cdot L \cdot cm^{-1}$, in water, Mw: 630): 271 nm (13332), 554 nm (317), 639 nm (327).

IR (KBr pellet): 3419 br, 2923m, 1606m, 1565m, 1499w, 1461s, 1396s, 1340m, 1288w, 1159w, 1076w, 1057w, 1036m, 1007m, 915w, 778w, 744w, 682m, 613m $cm^{-1}$.

UPLC analysis confirmed the trace amount of free $[H_2(Me_4\text{-}DTNE)]Cl_2$.

Water analysis (Karl-Fischer method): Anal. calcd. for $[(Mn_2(\mu\text{-}O)_2(\mu\text{-}OAc)(Me_4\text{-}DTNE)]Cl_2 \cdot H_2O$: 2.86%; Found: 4.71%.

2.2 Methanol as Solvent

Methanol: 10 mL: a green powder was obtained showing UV-Vis purity of 99%, and the yield of 102.9%.

UV-Vis spectrum ($\epsilon$: $mol^{-1} \cdot L \cdot cm^{-1}$, in water, Mw: 630): 271 nm (13388), 554 nm (308), 639 nm (318).

Anal. calcd. for $[Mn_2O_2(CH_3COO)(C_{18}H_{40}N_6)]Cl_2 \cdot H_2O$ $(C_{20}H_{45}Cl_2Mn_2N_6O_5)$: C, 38.11; H, 7.20; N, 13.33. Found: C, 38.33; H, 7.63; N, 12.57%.

IR (KBr pellet): 3425 br, 2923m, 1642m, 1568m, 1499w, 1462s, 1395s, 1337m, 1286w, 1159m, 1076m, 1055m, 1033m, 1004m, 912m, 780w, 744w, 678m, 613m $cm^{-1}$.

MS-ES$^+$: m/e 270.6.

UPLC analysis confirmed the trace amount of free $[H_2(Me_4\text{-}DTNE)]Cl_2$ in the Mn complex.

Total chloride amount was 11.07%.

Water analysis (Karl-Fischer method): Anal. calcd. for $[(Mn_2(\mu\text{-}O)_2(\mu\text{-}OAc)(Me_4\text{-}DTNE)]Cl_2 \cdot H_2O$: 2.86%; Found: 3.80%.

2.3 Dichloromethane as Solvent.

Dichloromethane: 20 mL: a green powder was obtaining of a UV-Vis purity of 101%, and the yield of 95.6%.

UV-Vis spectrum ($\epsilon$: $mol^{-1} \cdot L \cdot cm^{-1}$, in water, Mw: 630): 271 nm (13114), 554 nm (314), 639 nm (340).

IR (KBr pellet): 3426 br, 2926m, 1636m, 1564s, 1499w, 1462s, 1397s, 1341m, 1288w, 1159w, 1076m, 1055m, 1038m, 1001m, 916w, 778w, 744w, 682m, 614m $cm^{-1}$.

UPLC analysis confirmed the trace amount of free $[H_2(Me_4\text{-}DTNE)]Cl_2$ in the Mn complex.

Total chloride amount was 10.19%.

Water analysis (Karl-Fischer method): Anal. calcd. for $[(Mn_2(\mu\text{-}O)_2(\mu\text{-}OAc)(Me_4\text{-}DTNE)]Cl_2 \cdot H_2O$: 2.86%; Found: 1.92%.

2.4 Acetonitrile as Solvent.

Acetonitrile: 10 mL: a green powder was isolated having a UV-Vis purity of 85.3%, and the isolated yield of 87.2%.

UV-Vis spectrum ($\epsilon$: $mol^{-1} \cdot L \cdot cm^{-1}$, in water, Mw: 630): 271 nm (11345), 554 nm (265), 639 nm (280).

IR (KBr pellet): 3433 br, 2923m, 1642m, 1567m, 1499w, 1460m, 1396m, 1341w, 1058m, 1033m, 1004w, 912w, 780w, 744w, 678w, 613w $cm^{-1}$.

UPLC analysis confirmed the trace amount of free $[H_2(Me_4\text{-}DTNE)]Cl_2$ in the Mn complex.

Total chloride amount was 14.07%.

Water analysis (Karl-Fischer method): Anal. calcd. for $[(Mn_2(\mu\text{-}O)_2(\mu\text{-}OAc)(Me_4\text{-}DTNE)]Cl_2 \cdot H_2O$: 2.86%; Found: 1.39%.

2.5 Acetone as Solvent.

Acetone: 30 mL: yielding a green powder having a UV-Vis purity of 88.1%, and the isolated yield of 83.6%.

UV-Vis spectrum ($\epsilon$: $mol^{-1} \cdot L \cdot cm^{-1}$, in water, Mw: 630): 271 nm (11977), 554 nm (289), 639 nm (266).

IR (KBr pellet): 3426 br, 2924m, 1635s, 1560s, 1499w, 1458s, 1395s, 1338m, 1286w, 1183w, 1075m, 1056m, 1033m, 1003m, 985m, 913w, 780w, 744w, 678m, 616m $cm^{-1}$.

UPLC analysis confirmed the trace amount of free $[H_2(Me_4\text{-}DTNE)]Cl_2$ in the Mn complex.

Total chloride amount was 9.49%.

Water analysis (Karl-Fischer method): Anal. calcd. for $[(Mn_2(\mu\text{-}O)_2(\mu\text{-}OAc)(Me_4\text{-}DTNE)]Cl_2 \cdot H_2O$: 2.86%; Found: 2.66%.

2.6 Tetrahydrofuran (THF) as Solvent.

THF: 40 mL: yielding a green powder of a UV-Vis purity of 70.8%, and the isolated yield of 62.3%.

UV-Vis spectrum ($\epsilon$: $mol^{-1} \cdot L \cdot cm^{-1}$, in water, Mw: 630): 271 nm (8921), 554 nm (231), 639 nm (233).

IR (KBr pellet): 3422 br, 2924m, 1604s, 1567s, 1498w, 1463s, 1395s, 1337m, 1294w, 1159w, 1057m, 1032m, 1004m, 986m, 911w, 779w, 744w, 677m, 613m $cm^{-1}$.

UPLC analysis confirmed the trace amount of free $[H_2(Me_4\text{-}DTNE)]Cl_2$ in the Mn complex.

Total chloride amount was 10.51%.

Water analysis (Karl-Fischer method): Anal. calcd. for $[(Mn_2(\mu\text{-}O)_2(\mu\text{-}OAc)(Me_4\text{-}DTNE)]Cl_2 \cdot H_2O$: 2.86%; Found: 1.53%.

In all examples 2.1-2.6, the level of uncomplexed free ligand is below detection limit. Especially in ethanol, methanol and dichloromethane, the isolated yields and purities are much higher than the benchmarks (1.1 and 1.2). In all cases the removal of the solvent was much easier than in the benchmark experiments, facilitating the isolation of solid material.

Example 3

Preparation of $[(Mn_2(\mu\text{-}O)_2(\mu\text{-}OAc)(Me_4\text{-}DTNE)]Cl_2$ Dissolved in an Organic Solution Under $N_2$, to $Me_4$-DTNE (95% purity, 4 mmol) in different solvents (10 mL to 20 mL), solid mixture of $MnCl_2$ (99% purity, 8.8 mmol) and sodium acetate (99% purity, 2 mmol) were added. The mixture was stirred for 30 min at 58° C. After another stirring for 10 min cooled in an ice water bath, the freshly prepared mixture of 1 M of $H_2O_2$ in water (9 mL, 9 mmol) and 5 M of NaOH (1.35 mL, 6.75 mmol) was added drop-wise over 10 min. The mixture turned immediately dark green-brown. The mixture was stirred for 20 min in an ice water bath and then for 20 min at room temperature. Glacial acetic acid (2.5 mmol) was added. After stirring for another 20 min, the mixture was filtered to remove brown solid and the filtering bed was washed with solvents. Then the mixture reached 20 mL to 40 mL by adding solvents. From this green solution, a 40 (or 50) times dilution and a 1600 (or 2000) times dilution were made; and from the absorption in the UV-Vis spectrum at the wavelengths of 244 nm, 554 nm, and 639 nm, the concentration in the stock and the conversion were calculated, based on the molar extinction coefficient of $[Mn_2(\mu\text{-}O)_2(\mu\text{-}OAc)(Me_4\text{-}DTNE)]Cl_2$ with Mw 612) in water for 100% pure, $\epsilon$ (mol$^{-1}$·L·cm$^{-1}$): 271 nm (13200 mol$^{-1}$·L·cm$^{-1}$), 554 nm (315 mol$^{-1}$·L·cm$^{-1}$), 639 nm (325 mol$^{-1}$·L·cm$^{-1}$).

3.1 Ethylene Glycol as Solvent.

Ethylene glycol: 10 mL; the volume of the solution contained catalyst: 28 mL; diluted times: 50 times and 2000 times; UV-vis extinction:
271 nm: 1.052
554 nm: 0.905
639 nm: 0.869

So, the average UV-Vis conversion was 101.4%; the solution contained 8.01% (wt %) of the catalyst with the density of 1.112 g/mL.

UPLC analysis confirmed the trace amount of free $[H_2(Me_4\text{-}DTNE)]Cl_2$ in the Mn complex.

Total chloride amount was 1.89%.

3.2 1,2-Propylene Glycol as Solvent.

1,2-Propylene glycol: 10 mL; the volume of the solution contained catalyst: 40 mL; diluted times: 40 times and 1600 times; UV-vis extinction:
271 nm: 0.937
554 nm: 0.832
639 nm: 0.860

So, the average UV-Vis conversion was 107.1%; the solution contained 6.18% (wt %) of the catalyst with the density of 1.074 g/mL.

UPLC analysis confirmed the trace amount of free $[H_2(Me_4\text{-}DTNE)]Cl_2$ in the Mn complex.

Total chloride amount was 1.35%.

3.3 1,3-Propylene Glycol as Solvent.

1,3-Propylene glycol: 10 mL; the volume of the solution contained catalyst: 35 mL; diluted times: 40 times and 1600 times; UV-vis extinction:
271 nm: 1.048
554 nm: 0.990
639 nm: 1.040

So, the average UV-Vis conversion was 110.5%; the solution contained 7.23% (wt %) of the catalyst with the density of 1.075 g/mL.

UPLC analysis confirmed the trace amount of free $[H_2(Me_4\text{-}DTNE)]Cl_2$ in the Mn complex.

Total chloride amount was 1.60%.

3.4 Dimethyl Formamide (DMF) as Solvent.

DMF: 10 mL; the volume of the solution contained catalyst: 30 mL; diluted times: 40 times and 1600 times; UV-vis extinction:
271 nm: 1.295
554 nm: 1.152
639 nm: 1.120

So, the average UV-Vis conversion was 109.4%; the solution contained 8.66% (wt %) of the catalyst with the density of 1.039 g/mL.

UPLC analysis confirmed the trace amount of free $[H_2(Me_4\text{-}DTNE)]Cl_2$ in the Mn complex.

Total chloride amount was 1.80%.

3.5 Dimethyl Sulfoxide (DMSO) as Solvent.

DMSO: 20 mL; the volume of the solution contained catalyst: 40 mL; diluted times: 40 times and 1600 times; UV-vis extinction:
271 nm: 0.625
554 nm: 0.744
639 nm: 0.680

So, the average UV-Vis conversion was 82.9%; the solution contained 4.60% (wt %) of the catalyst with the density of 1.125 g/mL.

UPLC analysis confirmed the trace amount of free $[H_2(Me_4\text{-}DTNE)]Cl_2$ in the $[Mn_2(\mu\text{-}O)_2(\mu\text{-}OAc)(Me_4\text{-}DTNE)]Cl_2$ solutions.

Total chloride amount was 1.12%.

In all examples 3.1-3.5, the complex dissolved in an organic solvent was prepared readily. The level of uncomplexed free ligand was in all cases below the detection limit.

The most preferred solvents, ethylene glycol, 1,2-propylene glycol and 1,3-propylene glycol can be readily used to mix with other solutions (e.g. water, surfactant containing formulations, for various applications, such as domestic and industrial cleaning, textile treatment, etc.

Example 4

Preparation of $[Mn_2(\mu O)_2(\mu\text{-}OAc)(Me_4\text{-}DTNE)]Cl_2$ Complexation in Non-Aqueous Solutions, Isolation in Aqueous Solutions Under $N_2$, to $Me_4$-DTNE (95% purity, 4 mmol) in different solvents, solid mixture of $MnCl_2$ (99% purity, 8.8 mmol) and sodium acetate (99% purity, 2 mmol) were added. The mixture was stirred for 30 min at 58° C. for toluene or 40° C. for $CH_2Cl_2$. The mixture was then cooled in an ice water bath and stirred for another 10 min. The freshly prepared mixture of 1 M of $H_2O_2$ in water (9 mL, 9 mmol) and 5 M of NaOH (1.35 mL, 6.75 mmol) was added drop-wise over 10 min. The mixture turned immediately dark green-brown. The mixture was stirred for 20 min in an ice water bath and then for 20 min at room temperature. Glacial acetic acid (2.5 mmol) was added. After stirring for another 20 min, the mixture was filtered to remove brown solid and the filtering bed was washed with water. The filtrate divided into two layers. The water layer was then separated directly through a separating funnel. Trace volatile was removed for 20 min in vacuum. The mixture reached 25 mL by adding millipore water. From this green solution, a 50 times dilution and a 2000 times dilution were made; and from the absorption in the UV-Vis spectrum at the wavelengths of 244 nm, 554 nm, and 639 nm, the concentration in the stock and the conversion were calculated, based on the molar extinction coefficient of $[(Mn_2(\mu\text{-}O)_2(\mu\text{-}OAc)(Me_4\text{-}DTNE)]Cl_2$ with Mw 612 in water for 100% pure, $\epsilon$ (mol$^{-1}$·L·cm$^{-1}$): 271 nm (13200 mol$^{-1}$·L·cm$^{-1}$), 554 nm (315 mol$^{-1}$·L·cm$^{-1}$), 639 nm (325 mol$^{-1}$·L·cm$^{-1}$).

4.1 Toluene as Solvent.

Toluene: 30 mL; the volume of the solution contained catalyst: 25 mL; diluted times: 50 times and 2000 times; UV-vis extinction:
271 nm: 0.924
554 nm: 0.883
639 nm: 0.901

So, the average UV-Vis conversion was 86.1%; the aqueous solution contained 8.21% (wt %) of the catalyst with the density of 1.041 g/mL.

UPLC analysis confirmed the trace amount of free $[H_2(Me_4\text{-}DTNE)]Cl_2$.

Total chloride amount was 2.19%.

4.2 Dichloromethane as Solvent.

$CH_2Cl_2$: 30 mL; the volume of the solution contained catalyst: 25 mL; diluted times: 50 times and 2000 times; UV-vis extinction:
271 nm: 1.162
554 nm: 1.059
639 nm: 1.090

So, the average UV-Vis conversion was 106.4%; the aqueous solution contained 10.43% (wt %) of the catalyst with the density of 1.043 g/mL.

UPLC analysis confirmed the trace amount of free [H$_2$(Me$_4$-DTNE)]Cl$_2$.

Total chloride amount was 2.51%.

Both examples above show that complexation in a non-aqueous solvent that is poorly miscible with water, and then extracting the complex into water, furnishes the desired complex, again with low level of uncomplexed ligand present. Especially dichloromethane proved to be a suitable solvent, similar to what has been shown already in example 2.3.

Example 5

Preparation of Solid [Mn$_2$(µ-O)$_2$(µ-OAc)(Me$_4$-DTNE)](PF$_6$)$_2$

Under N$_2$, to Me$_4$-DTNE (95% purity, 10 mmol) in solvents, solid mixture of MnCl$_2$.4H$_2$O (22 mmol) and NaAc (5 mmol) were added. The mixture was stirred for 30 min at 58° C. After another stirring for 10 min cooled in an ice water bath, the freshly prepared mixture of 1 M of H$_2$O$_2$ in water (22.5 mL, 22.5 mmol) and 5 M of NaOH (3.375 mL, 16.875 mmol) was added drop-wise over 5 min. The mixture turned immediately dark green-brown. The mixture was then stirred for 20 min in an ice water bath and then for 20 min at room temperature. Glacial acetic acid (6.25 mmol) was added. After stirring for another 20 min, an aqueous of KPF$_6$ (30 mmol) in 75 mL of mQ water was added. 50 mL of acetonitrile was added to dissolve the green precipitate 5 min later. After stirring for another 10-15 min, the mixture was filtered to remove brown solid and the filtering bed was washed with acetonitrile. Then the mixture reached 260 mL or 170 mL by adding acetonitrile. All solvents in the green solution were evaporated (the water bath temperature <45° C.). The dark green residue was coevaporated with ethanol and ethyl acetate to facilitate the removal of most of the remaining water. The dark green residue was taken up in acetonitrile (125 mL), and the insoluble white salts separated by filtration were washed with acetonitrile. The partial evaporation of acetonitrile, water (50 mL) was added, and then the remainder of acetonitrile evaporated to leave a green solid and a little bit water. The suspension was put in a −25° C. fridge overnight, and was filtered off. The green solid was washed with cold water, ethanol, and n-hexane, and dried under vacuum at 45° C. for 5 hrs to afford dark green powder as [(Mn$_2$(µ-O)$_2$(µ-OAc)(Me$_4$-DTNE)](PF$_6$)$_2$.

5.1 EtOH/H$_2$O (2:1, v/v) as Solvent (Benchmark, Procedure According to Prior Art)

Ethanol/water (2:1, v/v): 100 mL. Green powder isolated, UV-Vis purity of 95.9%, and the isolated yield of 72.3%.

UV-Vis spectrum (ε: mol$^{-1}$·L·cm$^{-1}$, in acetonitrile, Mw 831): 271 nm (15442), 554 nm (342), 639 nm (387).

Anal. calcd. for C$_{20}$H$_{43}$F$_{12}$Mn$_2$N$_6$O$_4$P$_2$: C, 28.89; H, 5.21; N, 10.11. Found: C, 28.79; H, 5.21; N, 10.25%.

IR (KBr pellet): 3441 br, 2933m, 1633m, 1561m, 1499w, 1467m, 1384m, 1341m, 1287w, 1159w, 1077m, 1057m, 1035m, 1005m, 985m, 840vs, 780w, 743w, 692m, 679m, 608m, 558m cm$^{-1}$.

UPLC analysis confirmed the trace amount of free [H$_2$(Me$_4$-DTNE)](PF$_6$)$_2$.

The water amount was 1.78% by Karl-Fischer method.

5.2 Ethanol as Solvent.

Ethanol: 25 mL; green powder isolated, UV-Vis purity of 98.6%, and the isolated yield of 85.9%.

UV-Vis spectrum (ε☐: mol$^{-1}$·L·cm$^{-1}$, in acetonitrile, Mw: 831): 271 nm (16041), 554 nm (351), 639 nm (396).

Anal. calcd. for C$_{20}$H$_{43}$F$_{12}$Mn$_2$N$_6$O$_4$P$_2$: C, 28.89; H, 5.21; N, 10.11. Found: C, 28.77; H, 5.22; N, 10.19%.

IR (KBr pellet): 3441 br, 2933m, 1633m, 1562m, 1499w, 1467m, 1384m, 1342m, 1287w, 1159w, 1078m, 1058m, 1036m, 1005m, 986m, 840vs, 780w, 743w, 692m, 679m, 608m, 558m cm$^{-1}$.

MS-ES$^+$: m/e 270.6.

UPLC analysis confirmed the trace amount of free [H$_2$(Me$_4$-DTNE)](PF$_6$)$_2$.

The water amount was 0.55% by Karl-Fischer method.

Example 5.2 shows that in ethanol as solvent a higher yield/purity of solid [Mn$_2$(µ-O)$_2$(µ-OAc)(Me$_4$-DTNE)](PF$_6$)$_2$ has been obtained as compared to the product isolated from the water/ethanol mixture (comparative example 5.1).

Example 6

Preparation of [Mn$_2$(µ-O)$_3$(Me$_3$-TACN)]Cl$_2$.3H$_2$O

Under N$_2$, the mixture of Me$_3$-TACN (99% purity, 10 mmol), manganese(II)chloride (11 mmol) in either 20 mL water (6.1) or 20 mL ethanol (6.2) was stirred for 20 min at 35° C. After another stirring for 10 min cooled in an ice water bath, a freshly prepared mixture of 1 M H$_2$O$_2$ (12.5 mmol) and 5 M NaOH (15 mmol) was added dropwise over 5-10 min. The mixture turned immediately dark brown/red. The mixture was further stirred for 20 min in an ice bath and for another 40 min at room temperature. 1 M HCl (5.2 mmol) was added and stirred for 30 min in order to adjust pH value to 5. The red-wine mixture was filtered to remove brown solid and the filtering bed was washed with ethanol. The filtrate was reduced in vacuo (water bath: 35° C.-40° C.) to afford a red-oil. The residue was dissolved in ethanol, and the insoluble white salts separated by filtration were washed with ethanol. The ethanol filtrate combined was evaporated to dryness obtaining a red-oil. The red-oil was washed with acetonitrile and ethyl acetate until obtaining red solid, which was dried in vacuum at 45° C. for 6 hrs to afford red solid as [Mn$_2$(µ-O)$_3$(Me$_3$-TACN)$_2$]Cl$_2$.3H$_2$O.

6.1: Water as complexation solvent. Red powder, UV-Vis purity of 92.7%, and the yield of 88%.

UV-Vis spectrum (ε☐: mol$^{-1}$·L·cm$^{-1}$, in water, Mw 625): 244 nm (18016), 278 nm (17190), 313 nm (11069), 389 nm (949), 485 nm (355).

UPLC analysis confirmed the trace amounts of free [H$_2$(Me$_3$-TACN)]Cl$_2$.

Total chloride amount was 12.35%.

6.2 Ethanol as complexation solvent.

Red powder, UV-Vis purity of 92.9%, and the yield of 82%.

UV-Vis spectrum (ε☐: mol$^{-1}$·L·cm$^{-1}$, in water, Mw 625): 244 nm (18048), 278 nm (17231), 313 nm (11113), 389 nm (979), 485 nm (370).

UPLC analysis confirmed the trace amounts of free [H$_2$(Me$_3$-TACN)]Cl$_2$.

Total chloride amount was 11.83%.

The results shown in sections 6.1 and 6.2 indicated that both solvents (aqueous vs non-aqueous solvents) are suitable to form complex, whilst the non-aqueous solvent exhibits the advantage that the non-aqueous solvent may be easier removed by evaporated than the aqueous solvent.

We claim:

1. A powder comprising a manganese catalyst from a ligand of formula (I):

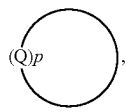

wherein:

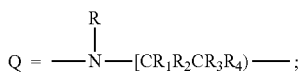

p is 3;
R is independently selected from the group consisting of hydrogen, C1-C6-alkyl, $CH_2CH_2OH$, and $CH_2COOH$, or one of R is linked to the N of another Q via an ethylene bridge;
$R_1$, $R_2$, $R_3$, and $R_4$ are independently selected from the group consisting of H, C1-C4-alkyl, and C1-C4-alkylhydroxy; and
wherein the power is obtained by spray drying or freeze drying.

2. The powder according to claim 1, wherein R is independently selected from the group consisting of $CH_3$, $C_2H_5$, $CH_2CH_2OH$, and $CH_2COOH$.

3. The powder according to claim 1, wherein $R_1$, $R_2$, $R_3$, and $R_4$ are independently selected from the group consisting of H and Me.

4. The powder according to claim 1, wherein the ligand is selected from the group consisting of 1,4,7-trimethyl-1,4,7-triazacyclononane ($Me_3$-TACN) and 1,2-bis-(4,7-dimethyl-1,4,7-triazacyclonon-1-yl)-ethane ($Me_4$-DTNE).

5. The powder according to claim 1, wherein the manganese catalyst is a salt having a non-coordinating counter ion selected to provide a water solubility of at least 30 g/l at 20° C.

6. The powder according to claim 5, wherein the non-coordinating counter ion is selected from the group consisting of chloride, nitrate, benzoate, sulfate, and acetate.

7. The powder according to claim 1, wherein the powder is obtained by the following steps prior to spray drying or freeze drying:
(i) treating a 0.03 mmol/ml to 4 mmol/ml solution of the ligand in a solvent, with a manganese salt to form a complexation mixture, wherein the ratio of three nitrogen ring per ligand to a manganese salt is from 0.8:2 and the complexation mixture contains from 0 to 6 wt % of water;
(ii) treating the solution of step (i) with hydrogen peroxide or a source of hydrogen peroxide to provide from 1 to 10 mole $H_2O_2$ per mole of the manganese salt;
(iii) treating the solution of step (ii) with base to provide a solution having a pH of from 8 to 13; and
(iv) treating the solution of step (iii) with acid to provide a solution having a pH of from 4 to 9.

8. A method of synthesising a dinuclear manganese catalyst salt from a ligand of formula (I):

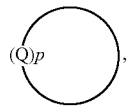

wherein:

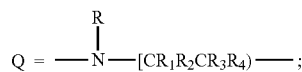

p is 3;
R is independently selected from the group consisting of hydrogen, C1-C6-alkyl, $CH_2CH_2OH$, and $CH_2COOH$, or one of R is linked to the N of another Q via an ethylene bridge;
$R_1$, $R_2$, $R_3$, and $R_4$ are independently selected from the group consisting of H, C1-C4-alkyl, and C1-C4-alkylhydroxy;
the method comprising the following steps:
(i) treating a 0.03 mmol/ml to 4 mmol/ml solution of the ligand in a solvent, with a manganese salt to form a complexation mixture, wherein the ratio of three nitrogen ring per ligand to a manganese salt is from 0.8:2 and the complexation mixture contains from 0 to 6 wt % of water;
(ii) treating the solution of step (i) with hydrogen peroxide or a source of hydrogen peroxide to provide from 1 to 10 mole $H_2O_2$ per mole of the manganese salt;
(iii) treating the solution of step (ii) with base to provide a solution having a pH of from 8 to 13;
(iv) treating the solution of step (iii) with acid to provide a solution having a pH of from 4 to 9.

9. The method according to claim 8, wherein R is independently selected from the group consisting of $CH_3$, $C_2H_5$, $CH_2CH_2OH$, and $CH_2COOH$.

10. The method according to claim 8, wherein $R_1$, $R_2$, $R_3$, and $R_4$ are independently selected from the group consisting of H and Me.

11. The method according to claim 8, wherein the ligand is selected from the group consisting 1,4,7-trimethyl-1,4,7-triazacyclononane ($Me_3$-TACN) and 1,2-bis-(4,7-dimethyl-1,4,7-triazacyclonon-1-yl)-ethane ($Me_4$-DTNE).

12. The method according to claim 8, wherein the non-aqueous solvent contains at least one OH group.

13. The method according to claim 12, wherein the non-aqueous protic solvent is selected from the group consisting of methanol, ethanol, 1-propanol, 2-propanol, 1-butanol, 2-butanol, iso-butanol, ethylene glycol, 1,3-propylene glycol, and 1,2-propylene glycol.

14. The method according to claim 8, wherein the salt comprises a non-coordinating counterion selected from the group consisting of chloride, nitrate, sulfate, acetate, and benzoate.

15. The method according to claim 8, wherein the method further comprises removing solvent from the solution resultant from step (iv) to provide a solid material.

16. The method according to claim 15, wherein the solvent is removed via spray drying, via freeze drying, or via evaporation at ambient or reduced pressure.

17. The method according to claim 15, wherein the solvent is removed via spray drying or via freeze drying.

18. The method according to claim 8, wherein after the complexation process of step (iv) water is added to the solution and the dinuclear manganese catalyst salt is extracted into the water to provide an aqueous catalyst solution and the solvent has a water miscibility in the range used from 0 to 20 g/L at 20° C.

19. The method according to claim 18, wherein the solvent for complexation is selected from toluene and dichloromethane.

20. The method according to claim 8, wherein when one of R is linked to the N of another Q via an ethylene bridge an alkali carboxylate or carboxylic acid is added before addition of hydrogen peroxide after step (i) and before step (ii).

21. The powder according to claim 7, wherein the manganese salt is a manganese (II) salt.

22. The powder according to claim 21, wherein the manganese catalyst is a dinuclear Mn(III) and/or Mn(IV) catalyst, and the solvent is a non-aqueous solvent.

23. The method according to claim 8, wherein the manganese salt is a manganese (II) salt.

24. The method according to claim 23, wherein the manganese catalyst is a dinuclear Mn(III) and/or Mn(IV) catalyst, and the solvent is a non-aqueous solvent.

* * * * *